Figure 1:
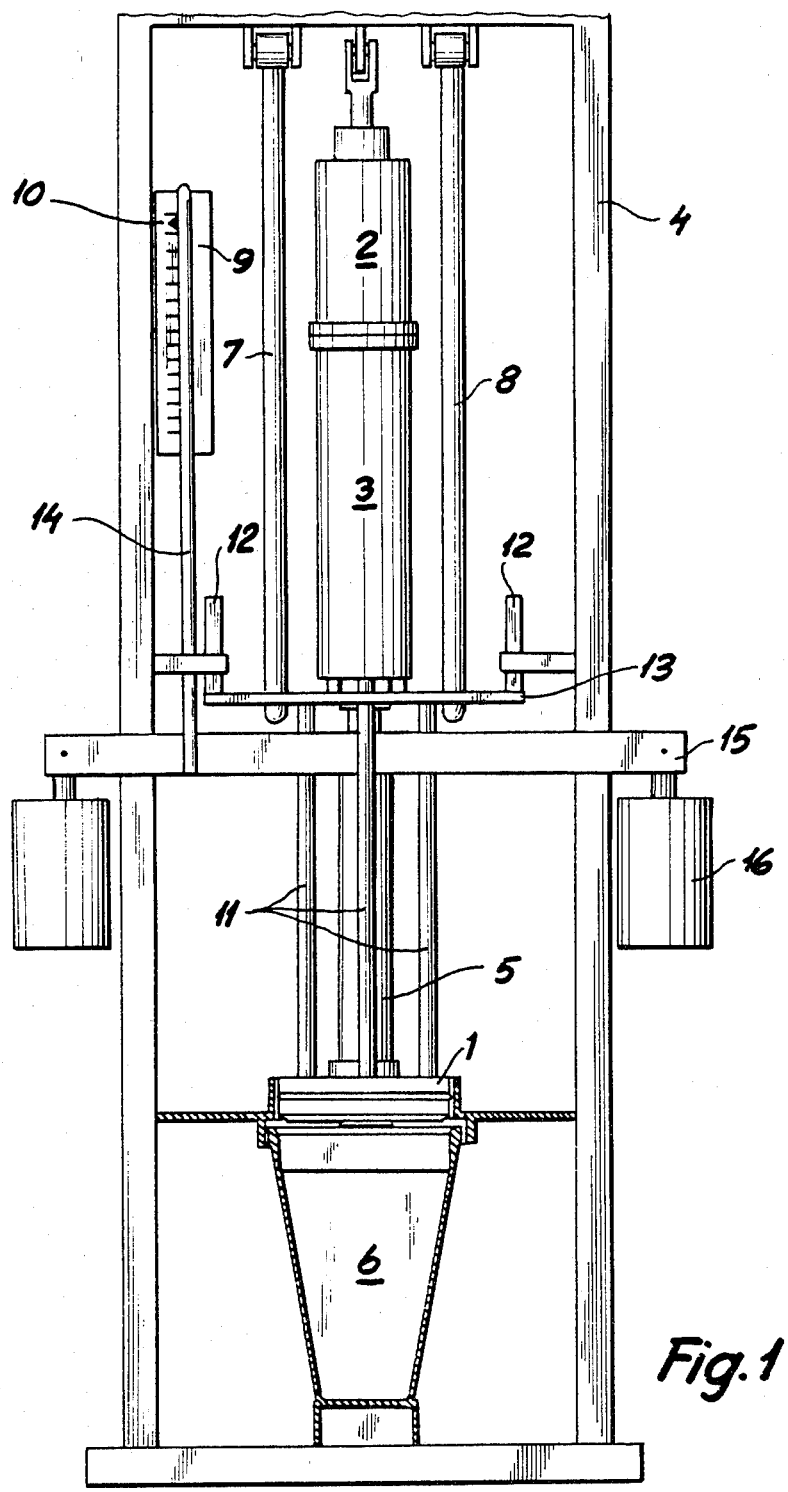

United States Patent [19]

Petersen

[11] 4,391,141

[45] Jul. 5, 1983

[54] APPARATUS FOR DETERMINING THE PROPERTIES OF A MATERIAL HAVING PLASTIC PROPERTIES BY DETERMINING ITS DENSITY

[75] Inventor: Olfert H. Petersen, Lejre, Denmark

[73] Assignee: Slagteriernes Forskningsinstitut, Roskilde, Denmark

[21] Appl. No.: 195,305

[22] Filed: Oct. 8, 1980

[30] Foreign Application Priority Data

Oct. 8, 1979 [DK] Denmark .............................. 4211/79

[51] Int. Cl.³ .......................... G01N 9/02; G01N 7/00
[52] U.S. Cl. .......................................... 73/433; 73/19; 73/149
[58] Field of Search .................. 73/433, 149, 32 R, 19, 73/37.5

[56] References Cited

U.S. PATENT DOCUMENTS

| | | | |
|---|---|---|---|
| 2,138,141 | 11/1938 | Cromer et al. ........................... | 73/19 |
| 2,141,977 | 12/1938 | Gray ....................................... | 73/19 |
| 3,282,115 | 11/1966 | Taylor et al. ..................... | 73/432 R |
| 3,585,861 | 6/1971 | Keng .................................... | 73/149 |

FOREIGN PATENT DOCUMENTS

4004/69  7/1969  Denmark .
2220110 11/1972 Fed. Rep. of Germany .
2608651  9/1977 Fed. Rep. of Germany .
1302657  1/1973 United Kingdom .

Primary Examiner—James J. Gill
Attorney, Agent, or Firm—Fleit, Jacobson & Cohn

[57] ABSTRACT

A method for determining the properties of a material having plastic properties, e.g. the fat content of minced meat or meat cut into pieces, comprises determination of the density of the material.

The measurement required for the determination of density is effected by means of a chamber which is substantially filled with the material and into which a displacement member is slidingly introduced through a hole in the wall of the chamber, said displacement member having a considerably smaller cross sectional area than the chamber. The displacement member is introduced so far into the chamber that the force of introduction applied reaches a predetermined value, and then the length of penetration of the member is recorded.

An apparatus for carrying out said method comprises a chamber (6) having a wall through which the displacement member of smaller cross sectional area than the chamber may be introduced, said displacement member being connected to means (3, 16, 9, 10) for pressing the unit into the chamber and indicating the length of penetration.

4 Claims, 2 Drawing Figures

APPARATUS FOR DETERMINING THE PROPERTIES OF A MATERIAL HAVING PLASTIC PROPERTIES BY DETERMINING ITS DENSITY

The invention relates to a method of determining the properties of a plastic or pliable material by determining its density on the basis of a measurement of weight and volume, said measurement of volume being effected by compressing a given quantity of material in a chamber.

In the meat industry there is a need for a reliable determination of the fat content of minced meat and whole meat products and accordingly also of the raw materials used. This will make it possible to observe the specific fat content limits laid down in various countries, while permitting the production of a product which is uniform in that respect, which is essential to marketing and industrial economy.

It is known that the fat content of a meat material is a function of the density of the meat material. However, the function varies with the type of meat, e.g. pork and beef, and fresh or treated, such as salted, and of the temperature of the meat material. This appears e.g. from the British Patent Specification No. 1 037 901 and the Danish Patent Applications No. 4004/69 and 2517/71. The devices and methods disclosed by them all rely on a measurement of density for the determination of the fat content of a meat material. This measurement of the density of the meat material is effected by placing a specific quantity of material, optionally weighed in a cylinder and compressing the meat material by a piston. This provides an indication of the volume of the meat material. The drawbacks of this determination of volume are the relatively poor accuracy and the relatively great force to be applied.

The object of the invention is to provide a method which allows a greater measure of accuracy and requires smaller forces than the known methods mentioned in the foregoing.

This object is achieved according to the invention by a method which is characterized by the fact that said measurement of volume is effected by means of a displacement member whose cross sectional area is considerably smaller than the cross sectional area of the chamber, said displacement member being introduced so far into the chamber, substantially filled with the material, as to provide a desired pressure in the chamber at the termination of the introduction, and by recording the length of penetration of the displacement member in the chamber then obtained.

When carrying out the method of the invention the plastic or pliable material is placed in the chamber which is then closed.

According to the invention it is particularly expedient to keep the chamber air-tight during the introduction of the displacement member.

For accuracy, it is expedient to place a quantity of plastic or pliable material in the chamber corresponding to a degree of filling of a least 75%, preferably at least 90%.

The displacement member, which may be inserted through the wall of the chamber preferably in air-tight relationship therewith, is then subjected to a predetermined force so as to press the member a distance into the chamber while displacing a volume in it. When the displacement member is at rest there is a predetermined pressure in the chamber. According to the invention it is expedient to introduce the displacement member with a force that provides a pressure of 5 to 15 bars in the material, which greatly compresses the entrained air. This improves the accuracy.

According to the invention a displacement member capable of displacing up to 10-25% of the volume of the chamber should preferably be used for the greatest possible accuracy of the measurement to be achieved.

As displacement member may be used a cylindrical rod. The volume displaced is easy to determine as it is a linear function of the length of penetration. The weight of the quantity of material examined is then determined if it is not already determined.

In respect of non-compressible, ideal plastic or pliable materials and by using an air-tight closed chamber the density of the material, which may be other than meat and fat, may be expressed by:

$$\rho = \frac{M}{V - \frac{\Delta V \times P_2}{P_2 - P_1}}$$

M being the mass of the quantity, $P_1$ the initial pressure in the chamber, $P_2$ the predetermined pressure, V the initial volume of the chamber and $\Delta V$ the volume displaced. The properties of the material, e.g. fat content, may be conventionally determined from the density found with the usual adjustments. When the fat percentage is determined adjustments are made for temperature, type of animal, etc.

Weighing, measurement of displacement volume and determination of temperature and/or calculation thereof may optionally be made automatically, e.g. so that after the material is placed in the chamber the operative only has to read the fat percentage digitally.

In case of non-ideal, somewhat compressible materials, such as fat and meat, it may be expedient to find the property empirically by testing a plurality of equally heavy samples of known property, e.g. fat content, and marking the displacement member accordingly so as to provide a graduated scale which directly indicates the property of a specific weight quantity of sample.

A preferred embodiment of the method of the invention for determining the fat content and/or meat content of a mixture containing pieces of meat and fat is characterized by filling the chamber with the mixture and closing said chamber, introducing the displacement member into the chamber until the pressure in it has reached a predetermined value of between 5 and 15 bars, measuring the total penetration extent of the displacement member and optionally the temperature of the mixture, and using said measurements together with the weight of the mixture, which may be measured before, during and after said measurement of volume or is predetermined, for determining the composition of the mixture.

The invention also relates to an apparatus for carrying out the method of the invention, said apparatus comprising a chamber which serves to receive the plastic or pliable material and is provided with a means for applying a pressure in the material.

According to the invention such an apparatus is characterized in that said means comprises a displacement member which is slidably movable through the wall of the chamber and whose cross sectional area perpendicular to the direction of movement is smaller than the area of the chamber in the same plane, said member being connected to drive means arranged to apply a predetermined force towards the interior of the chamber and provided with measuring means arranged to indicate the penetration extent of the unit in the chamber.

According to the invention it is particularly expedient that the chamber is arranged to be kept air-tight during the introduction of the displacement member into it.

As explained in the foregoing in respect of the use of the apparatus for the carrying out of the present method, the cross sectional area of the member and the distance which its end may be introduced into the chamber should preferably be arranged to displace up to 10–25% of the volume of the chamber. According to the invention it is expedient that the displacement member is a preferably cylindrical rod which is preferably circular in cross section.

The diameter of the displacement member may e.g. be 0.5–0.1 time the diameter of the chamber, and the maximum penetration extent of the member is e.g. 1–0.5 time the greatest dimension of the chamber. This provides a very high degree of accuracy, and the penetration force applied becomes small.

In an advantageous embodiment of an apparatus of the present type the chamber may be shaped as an inverted truncated cone, and the displacement member may be a rod that may be passed through the upper side of the truncated cone into the chamber. This provides for rapid and easy emptying and cleaning of the apparatus.

Figure 2:
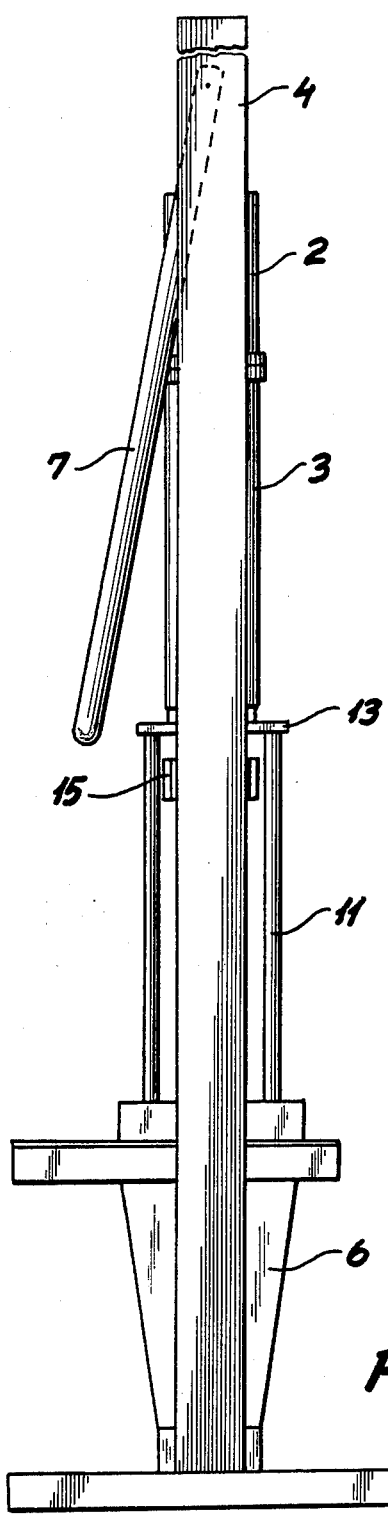

The invention will be explained more fully below by way of an embodiment of an apparatus for determination of fat in minced meat and meat cut into pieces with reference to the drawing, in which FIG. 1 shows, partly in section, an apparatus according to the invention, seen from the front, i.e. from the side of operation, and FIG. 2 is a side view of the apparatus without weights.

The apparatus comprises a cap 1 which is secured to the piston housing of two pneumatic cylinders 2 and 3 by means of rods 11 and a plate 13 provided with guide means 12. The piston rod in the upper cylinder 2 is connected to a frame 4 so that the piston housing and the cap 1 may be moved up and down. The piston rod in the lower cylinder 3 is attached to a displacement rod 5 which may be moved up and down through an opening in the cap in sealing engagement therewith. A bracket 15 for the attachment of weights 16 is secured to the displacement rod. Below the cap is mounted a container 6 whose inside diameter at the top corresponds to the outside diameter of the cap 1 so that the cap may slide in the upper portion of the container in air-tight relationship therewith.

On the frame 4 there are two pivotable rods 7 and 8, which in one active position are vertical, and in another inactive position inclined (as shown in FIG. 2). There are also a scale 9 and a pointer 10 which follows the up and down movement of the displacement rod 5 via a connecting member 14.

The apparatus is also provided with a not shown pneumatic control device, and moreover there are means for inserting the container 6 below the cap 1 and maintaining it in proper position below the cap.

The fat content of a sample of minced meat or meat cut into pieces is measured in the following manner:

The container 6 containing a predetermined weight quantity of sample, preferably approx. 6 kg, is placed, after shaking, below the cap 1 and placed in proper position. The cap 1 is then moved in air-tight relationship down in the container by means of the cylinder 2 and so far that the rods 7, 8 are pivoted into a vertical position. The displacement rod 5 is pressed downwards by means of a pressure in the cylinder 3. Alternatively, the pressure in the cylinder may be balanced, weights 16 suspended from the bracket forcing the displacement member 5 downwards. This provides for an increase in the pressure in the container 6, pressing the cap 1 somewhat upwards until the plate 13 engages the ends of the rods 7, 8.

The downward movement of the displacement rod 5 into the container 6 continues until the force acting on the rod from the pressure in the container 6 completely counteracts the force produced by the piston in the cylinder 3 or the weights 16. The pressure in the container 6 is e.g. 6 bars.

Then the fat content of the sample is read on the predetermined scale 10 opposite the pointer 9.

The displacement rod 5 is pulled up to its initial position by means of the cylinder 3, the rods 7, 8 are pivoted to the inclined position, the cap 1 is pulled out of the container 6 which is removed from the apparatus and is emptied, and then the apparatus is ready for the next measurement procedure.

In another embodiment the pointer and scale are replaced by a potentiometer whose movable arm follows the up and down movement of the displacement rod 5, and further a sample temperature sensor and a calculating unit which converts the values obtained electrically from the potentiometer and temperature sensor to a fat percentage. The calculating unit may be provided with switches for adjustment depending on e.g. types of meat and salting state. Optionally the calculating unit may also be connected to an electric weight which is used for the weighing of the quantity of minced meat or cut pieces of meat. In that case, it is not required to exactly weigh a predetermined quantity of minced meat; the container is merely filled with minced meat or cut pieces of meat and the weight in question is then electrically communicated to the calculating unit which calculates the density e.g. on the basis of the formula given above and find the fat percentage on the basis of the result.

The method and the apparatus of the invention may be used both in connection with the production of an expediently mixed batch and for continuous production control. Filling, measuring and recording may be effected fully automatically, so that e.g. at least two flows of minced meat can be currently monitored for percentage of fat (and optionally other properties, such as protein and water content as well as water absorption capacity). The values found may then control the feed rates of these flows of minced meat by means of a calculation unit, thereby to permit the currents to be united into a single flow which has a specific content of i.a. fat.

This provides for optimization taking into account statutory minimum and maximum requirements of the content of fat and possibly protein, water etc. of the finished product.

I claim:

1. An apparatus for determining the properties of a material having plastic properties by determining its density on the basis of a measurement of weight and volume, which comprises:

a chamber for receiving said material;
   a displacement member for contacting the material to thereby apply pressure to the material, which member is slidably movable through a wall of the chamber and has a cross sectional area perpendicular to the direction of movement smaller than the cross sectional area of the chamber in the cross section;

drive means connected to said member for applying a predetermined force on said displacement member towards the interior of the chamber, said drive means comprising means for applying a predetermined weight to said displacement member; and measuring means for measuring the penetration depth of the displacement member into the chamber to thereby determine the volume of the material, the measured volume and weight being used to determine density of the product.

2. An apparatus according to claim 1, further comprising means for maintaining the chamber substantially air-tight during the introduction of the displacement member into the chamber.

3. An apparatus according to claim 1, wherein the displacement member is a cylindrical rod.

4. An apparatus according to claim 1, wherein the displacement member comprises a cylindrical member having a circular cross section.

* * * * *